United States Patent [19]

Reinhardt et al.

[11] Patent Number: 4,790,751
[45] Date of Patent: Dec. 13, 1988

[54] DENTAL VIEWING APPARATUS AND METHOD

[75] Inventors: Richard A. Reinhardt, Roca; Gerald J. Tussing, Lincoln, both of Nebr.

[73] Assignee: The Board of Regents of the University of Nebraska, Lincoln, Nebr.

[21] Appl. No.: 119,201

[22] Filed: Oct. 30, 1987

Related U.S. Application Data

[63] Continuation of Ser. No. 805,826, Dec. 6, 1985, abandoned.

[51] Int. Cl.$^4$ .............................................. A61C 3/00
[52] U.S. Cl. ...................................... 433/29; 433/31; 433/80; 433/140; 433/215
[58] Field of Search ................. 433/29, 30, 31, 80, 433/81, 82, 83, 140, 215

[56] References Cited

U.S. PATENT DOCUMENTS

| | | | |
|---|---|---|---|
| 2,066,313 | 1/1937 | Barr | 433/29 |
| 3,032,879 | 5/1962 | Lafitte | 433/29 |
| 3,352,305 | 11/1967 | Freedman | 433/31 |
| 4,014,098 | 3/1977 | Scrivo et al. | 433/29 |
| 4,020,556 | 5/1977 | Sotman | 433/29 |
| 4,116,239 | 9/1978 | Ewen | 433/80 |
| 4,519,780 | 5/1985 | Strohmaier et al. | 433/29 |
| 4,619,612 | 10/1986 | Weber et al. | 433/29 |
| 4,629,425 | 12/1986 | Detsch | 433/31 |

FOREIGN PATENT DOCUMENTS

1280339  7/1972  United Kingdom .................. 433/29

OTHER PUBLICATIONS

"Illumination of the Oral Cavity", Taylor, et al., J. Am. Dent. Assoc. 74(5):1207-1209, 1967.
"Transillumination of the Oral Cavity with Use of Fiber Optics", Freedmann, et al., J. Am. Dent. Assoc. 80(4):801-809, 1970.
"Fiber Optic Lighting Systems": Their Role in Dentistry, Bomba, Dent. Clin. North Am. 15(1): 197-218, 1971.
"Fiber Optic Surgical Retractor", Plezia, R. A. et al., J. Oral Surg. 34(11):1038, 1976.
"Fiberoptic Light Sources and Handpieces", Leon, Quintessence Int. 14(9):923-928, 1983.
"Dental Fiberoptic Hand Pieces: Recommendations for Proper Use", Gildersleeve et al., J. Am. Dent. Assoc. 114(2):200-203, 1987.
"Fiberoptic Illumination in Radicular Restorations", Ecker, J. Prosthet. Dent. 55(4):433-434, 1986.
"A Comparison of Radiographic and Fibre-Optic Diagnosis of Approximal Caries Lesions", Purdell et al., Jour. of Dent., 2:143-148, 1974.
"Detection of Interproximal Caries by Transillumination", Schulein et al., Gen. Dent. 32:430-432, 1984.
"The Use of Fiber Optics Transillumination for the Detection of Proximal Caries", Barenie et al., Oral Surg. 36(6):891-897, 1973.
"Fiber Optics in Dentistry", Ehrlich, Dental Assistant, 10, 1969, p. 25.

(List continued on next page.)

Primary Examiner—John J. Wilson
Attorney, Agent, or Firm—Vincent L. Carney

[57] ABSTRACT

To permit more effective viewing during dental surgery or diagnosis, a retractor or probe assembly includes: (1) a cylindrical stainless steel handle about 14 centimeters long and 7 millimeters in diameter to which a mirror may be mounted; and (2) a 15 millimeter long retractor or probe extending at right angles to the handle with openings in it for the passage of light and an opening near the retractor or probe for water and air. One end of the handle opposite to the retractor or probe receives an air hose, a water hose and a fiber optic bundle connected to a dental light source to supply air, water and/or light to the retractor or probe end of the handle. The retractor or probe assembly: (1) supplies light with sufficient intensity for transillumination or direct illumination of the dental root, pulp chamber, or other constricted areas in the oral cavity: and (2) in the case of a blade shaped retractor, is strong enough to permit insertion into and retraction of the gingival tissue or other oral soft tissue.

6 Claims, 5 Drawing Sheets

OTHER PUBLICATIONS

"Fiber Optics Transillumination in Caries Diagnosis", Peltola et al. Proc. Finn. Dent. Soc. 1981, 77, pp. 240–244.

"Detection of Enamel Demineralization with Transillumination", Parker et al., Clinical Preventative Dent., V. 3, N. 3, May–Jun. 1981, pp. 12–14.

"Fiber Optic Lighting in Oral Surgery", Baurmash et al., N.Y. State D. J., V. 35, 1–1969, pp. 29–32.

"The use of Fiber Optics as a Diagnostic Aid", Friedman, Dental Survey 48:38–41, 1972.

"An Evaluation of Transillumination for Caries Detection in Primary Molars", Wright et al., J. of Dent. for Children, May–Jun. 1972, pp. 41–43.

"Transillumination in the Oral Cavity", Winter et al., Dental Digest, Mar. 1949, pp. 106–110.

"A Clinical Evaluation of Fiber Optics In Diagnosis", Reynolds et al., JSCDA, 11–1971, vol. 39, pp. 896–900.

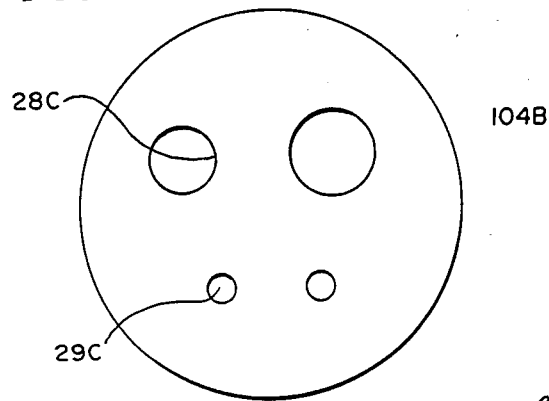
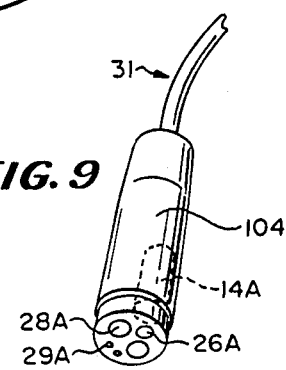
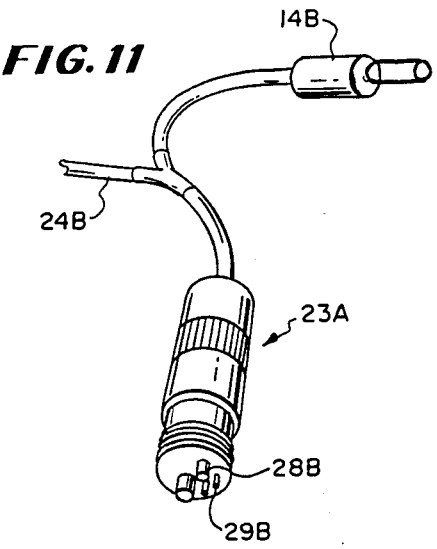
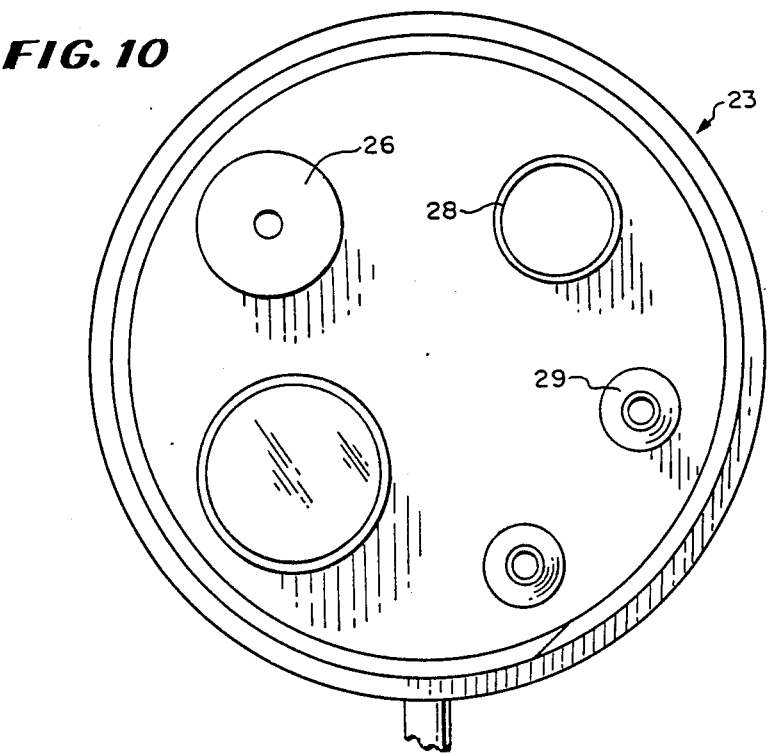

4,790,751

DENTAL VIEWING APPARATUS AND METHOD

This application is a continuation of application Ser. No. 805,826, filed Dec. 6, 1985, now abandoned.

BACKGROUND OF THE INVENTION

This invention relates to dental techniques and equipment.

In one class of dental technique, a retraction tool is used to retract the gingival tissue. A source of illumination, air and water are used to provide better visibility for planing and scaling accretions from the root surface such as by an ultrasonic scaling device. The gingival tissue is generally cut and retracted after certain preliminary procedures such as the application of a local anesthesia and the like.

In prior art devices used in this class of dental technique, separate devices are used for retractors, light sources, air sources and water sources, thus requiring a second person to hold and use one of the devices.

Such techniques have several disadvantages, such as: (1) it requires more than one person to perform the technnique on a patient; (2) it results in a significant amount of root accretions being left behind; (3) the root debridement takes a considerable amount of time and the results are not predictable because of the limited visual and mechanical access; (4) there is much soft tissue trauma and bone exposure trauma because the number and size of instruments involved require the reflection of an extensive mucoperiosteal flap for access; (5) there is much post-operative discomfort; (6) sutures must be used; (7) there must be post-operative visits to examine the gingival tissues and remove stitches and the like; (8) the soft tissue adapts poorly to the root; and (9) under some commonplace circumstances further surgical procedures are required.

SUMMARY OF THE INVENTION

Accordingly, it is an object of the invention to provide an improved surgical dental technique.

It is a further object of the invention to provide a novel method of improving visibility during certain surgical dental techniques as well as for diagnosis in certain constricted areas of the oral cavity.

It is a still further object of the invention to provide a novel dental probe.

It is a still further object of the invention to provide a novel dental probe that is capable of being used with one hand by a single dentist to retract gingival tissue and provide light and air to the dental surface while the dentist uses his other hand to work on the dental surface such as for scaling.

It is a still further object of the invention to provide a relatively small probe or retractor which supplies light and air and a retraction tool.

In accordance with the above and further objects of the invention, a probe assembly is provided which includes a relatively small rigid handle which may be held in one hand by an operator and a probe extending at right angles thereto. A source of light, a source of air and a source of water are supplied by light conductors and hoses respectively to the retractor assembly with both light conductors and hoses being supported by the handle and providing illumination and air or water clearing of the dental area on which work is being done. For transillumination, the light conductors supply at least 3.5 milliwatts of light per square millimeter close enough to a surface of the tooth to transmit light through the dentin within the tooth which is some distance away from the tooth surface which in turn allows detection of accretions or irregulatiries, caries, fractures, etc. on the tooth surface.

The dental tool (probe or retractor) is between 3 and 30 millimeters long and may be either a blade shaped retractor or cylindrical probe. If cylindrical, it has a diameter of between ¼ and 3 ½ millimeters and, if blade shaped, has: (1) a thickness of between ¼ and one millimeter; (2) a width of between ½ and ten millimeters; and (3) a length of between 3 and 30 millimeters. Control over the air supply and water are provided by the operator through either a button on the handle or a foot pedal, but generally with a foot pedal.

With this equipment, the dentist, after certain preliminary steps such as anesthesia and the like, may retract and reflect the gingival tissue away from the root of a tooth with one hand using the retractor, and supply light through the retractor and air and/or water focused at the retractor tip, while using the other hand to operate a scaling device such as an ultrasonic scaler. The light supplied is sufficient for examination of deposits on the tooth by transillumination or direct viewing.

From the above description, it can be understood that the technique of this invention has several advantages such as: (1) it can be performed by one person; (2) it requires less root planing skill because of better visual and mechanical access; (3) there is more predictable root debridement; (4) root debridement requires less time; (5) there is less soft tissue trauma to the gingival crevice lining because the tissue is held away from the scaling tip; (6) there is minimal post-operative discomfort; (7) no sutures or post-operative visits are usually required; (8) there is excellent soft tissue adaptation to the root; and (9) it may eliminate the need for more involved surgical procedures.

SUMMARY OF THE DRAWINGS

The above-noted and other features of the invention will be better understood from the following detailed description when considered with reference to the accompanying drawings in which:

FIG. 9 is a perspective view of one embodiment of an adaptor that serves as a connecting source for light, air and water useful in the apparatus for dental viewing of FIG. 1;

FIG. 10 is an end elevational view of the hose connector section of FIG. 2;

FIG. 11 is a plan view of another embodiment of the male connector of an adaptor;

FIG. 12 is a fragmentary side view of the female end of the tubing into which the male connector of FIG. 11 fits;

DETAILED DESCRIPTION

Figure 1:
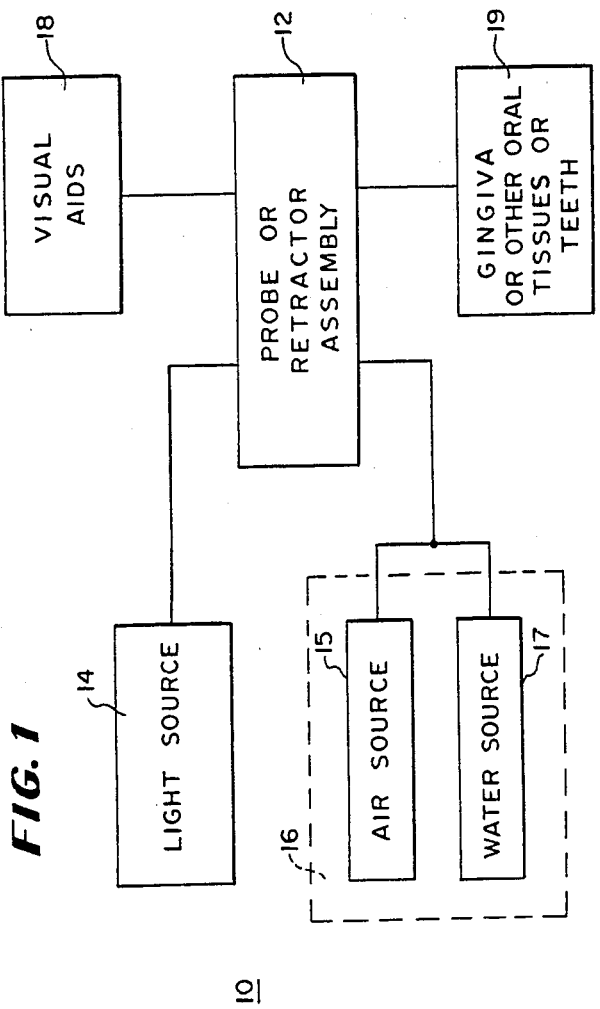
FIG. 1 is a block diagram of apparatus for dental viewing in accordance with the invention.

In FIG. 1, there is shown a block diagram of a dental viewing apparatus 10 having a probe assembly or retractor assembly 12, a light source 14, a fluid source 16, and certain visual aids 18 adapted to be used on the gingiva, teeth or other oral tissues of a patient indicated schematically at 19. The probe assembly 12 receives light from the light source 14 and fluid from the fluid source 16. In one embodiment, it supplies the light and fluid to the gingiva and teeth 19 while the gingiva is being retracted by the probe assembly so that planing or scaling of the tooth may be performed more effectively, sometimes in cooperation with certain visual aids 18.

The fluid source 16 includes a conventional source of air 15 and a conventional source of water 17 which are standard dental equipment. The air and water are the fluids connected to the probe or retractor assembly to be described hereinafter. The probe or retractor assembly is a dental instrument assembly which holds a dental tool point which may be a probe or a retractor depending on the need of the dentist.

The probe or retractor assembly 12 is constructed to be adaptable for positioning at different angles and locations to insert a probe or retractor into a dental cavity while applying sufficient light for conventional direct light dental techniques and transillumination dental techniques.

It applies sufficient light to identify by transillumination several characteristics of the teeth, such as: (1) calculus and other deposits on the root surface in the gingival sulcus; (2) calculus and other deposits on the root surface during minimal or complete gingival reflection in periodontal surgery; (3) margin-to-bone relationships during crown lengthening procedures; (4) cervical and subgingival caries; and (5) root fractures which are interproximal or within the pulp chamber and canal.

It provides sufficient direct light to: (1) identify calculus and other deposits on the root surface; (2) evaluate restoration margins; (3) permit visualization of root planing and scaling; and (4) permit photography. The probe or retractor is small enough and light is emitted from its tip so that other dental instruments or structures do not block complete illumination and visualization of confined oral areas.

The cylindrical probe design is small enough to be placed into pulp chambers or pulp canal orifices with sufficient remaining room to visualize and instrument: (1 1 ) calcifical canals; (2) fracture lines within the pulp chamber; and (3) internal and external resorption. The probe tip may also be placed into other small spaces (e.g., caries under crown margins) where reflected light will not reach.

For this purpose, the cylindrical probe must be small enough in diameter to fit within the access opening of a pulp chamber with another instrument such as a rotary bur and still leave sufficient space, such as the same amount of space to ten times the space occupied by the probe and other instrument. It should have a diameter in the range of 0.5 millimeters to 1.75 millimeters for endodontic use.

During illumination, the probe device supplies fluid such as air from an air hose to permit the removal of other fluids which might otherwise interfere with good visualization and may provide a water spray. During one process, the probe assembly may be used in retraction of the gingiva for better illumination and visualization and is adapted to be carried with one hand while serving these functions to permit use of the other hand to manipulate instruments such as planing curettes or ultrasonic cleaning instruments.

Figure 2:
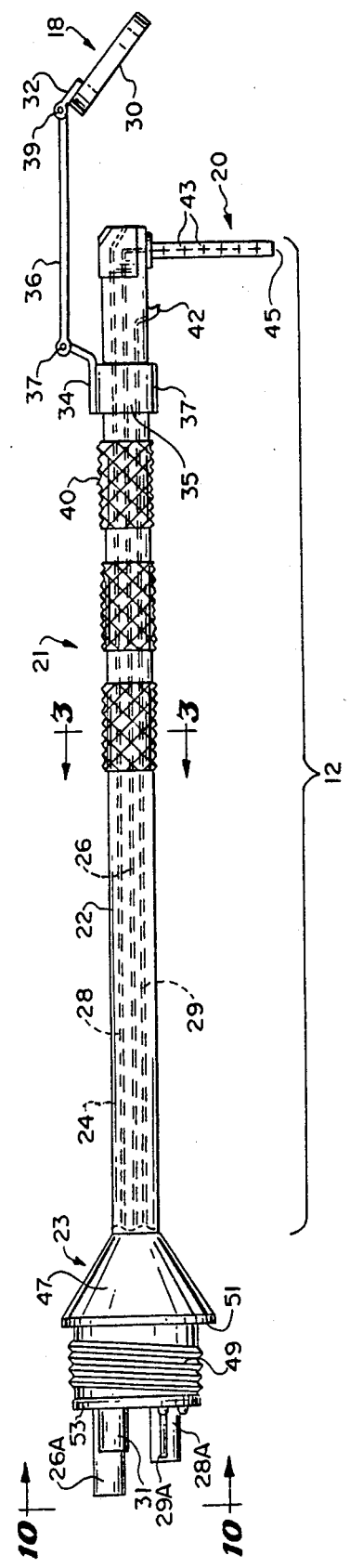
FIG. 2 is an elevational view of a probe assembly useful in an embodiment of the invention of FIG. 1.

In FIG. 2, there is shown a fragmentary elevational view of the probe assembly 12 and a visual aid 18. As shown in this view, the probe assembly 12 includes a cylindrical probe 20, a handle 21, and a hose connector section 23. The visual aid 18, the probe 20 and the hose section 23 are all mounted to the handle 21, which is stiff and may be held by the dentist when using the probe 20 to illuminate the root, pulp chamber or other constricted areas in the oral cavity while viewing the area with or without the visual aid 18. The hose connector section 23 communicates with the interior of the handle 21 in one embodiment to supply the mouth with: (1 1 ) air at a pressure above atmospheric pressure and at least 20 psi but normally 30 psi; (2) water; and (3) light with the light being transmitted through the retractor 20.

Figure 7:
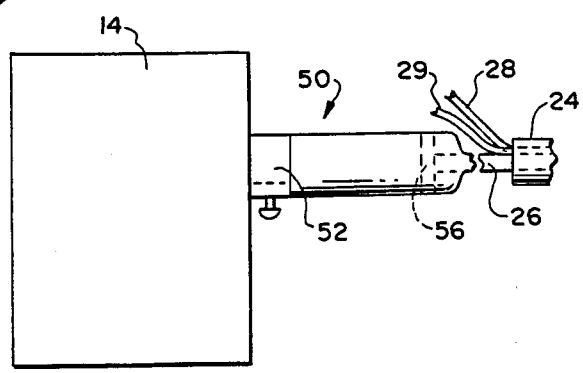
FIG. 7 is a simplified fragmentary elevational view of a light source and connector useful with the dental viewing apparatus of FIG. 1.

The handle 21, in this embodiment, includes a stiff cylindrical tubular sheath 22 extending to the hose connector section 23 which extends from the handle 21 to form a socket of standard configuration for connection to a flexible hose, preferably through a hose socket of standard configuration for the type now used to supply air, water and light to dental instruments. The handle 21 is, in this embodiment, hollow to contain the air hose 28, the water hose 29 and the light conductor bundle 26, which may be encased in a plastic sheath 24. In the preferred embodiment (FIGS. 7, 11 and 12), the handle 21 (FIGS. 2 and 4) does not extend to the socket as shown in FIG. 2 but instead the flexible hose 24B extends beyond the handle casing 22 at least three feet to the adaptor 23A (FIG. 11) and light source adaptor 50 (FIGS. 7 and 11).

The handle 21 includes on its surface a plurality of knurled portions, one of which is shown at 40, and in the preferred embodiment, is formed of stainless steel. In the preferred embodiment, the handle is at least 6 centimeters long, and no more than 25 centimeters long and preferably 14 centimeters long. It is cylindrical with a diameter of between 3 millimeters and 20 millimeters and is preferably 7 millimeters.

The visual aid 18 includes a mirror 30 having rounded corners, a mirror support 32, a mirror holder 36, and a holder support 34. In the embodiment shown in FIG. 2, the mirror 30 is attached at one end to a flat metal mirror holder 36, which extends generally parallel to the longitudinal axis of the handle 21, and by an angled mirror support 32 to extend beyond the probe 20. The mirror holder 36 is hinged at 37 and the mirror support 32 is hinged at 39 to permit up and down motion.

The other end of the flat metal mirror holder 36 is attached to the holder support 34 which is attached to a generally tubular flexible clamp that may be snapped over the handle 21 by bending the curved two half cylinder side portions apart and forcing them around the tubular handle. One of the two side portions is shown at 35. They are separated at the bottom 37 and attached to the mirror holder 36 at a flat portion at the top of the handle 21 (the bottom of the handle is the side from which the probe 20 extends). The curved portions have the same or a slightly smaller inner diameter than the outer diameter of the handle 21 to hold the mirror holder 35 in place or to allow it to be rotated around or moved longitudinally along the handle 21 with finger pressure. In the embodiment of FIG. 2, the mirror holder 35 may instead be welded or otherwise adhered in place.

Figure 3:
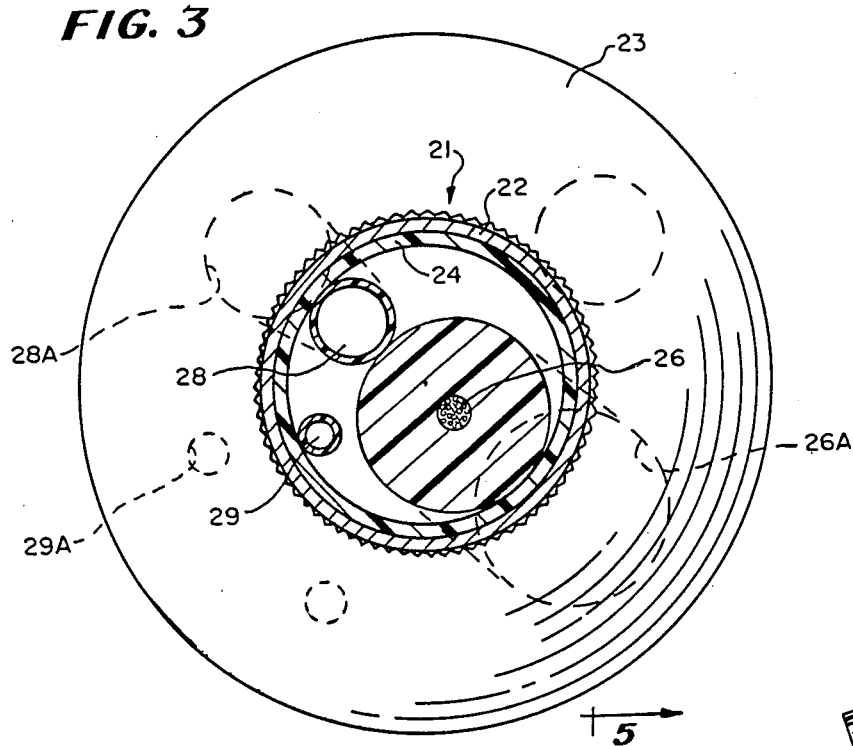
FIG. 3 is an enlarged sectional view taken through lines 3—3 of the probe assembly of FIG. 2.

In FIG. 3, there is shown a sectional view taken through lines 3—3 of FIG. 2 showing a portion of the handle 21 in section and a portion of an air, water and light tube formed by the sheath 24. As shown in this view, the steel casing 22 of the handle portion 21 encloses within it the light conductor 26, air hose 28 and water hose 29 which are within the handle and extend from one end of the handle at this retractor 20 and opening 42 (FIG. 2) and from the other end to the light and fluid sources 14 and 16 (FIG. 1).

In the preferred embodiment, the casing 22 is tubular, cylindrical and of stainless steel. It is sufficiently long to permit easy holding and manipulation by the dentist and has a sufficiently large inner diameter to accommodate the fluid hoses and light conductors. However, in some embodiments, it may consist of only a flexible plastic sheath fastened to a separate handle to be described hereinafter. In this embodiment, the terminal light guide is between 10 and 30 millimeters long and adapted to be inserted in a handle to be manipulated by the dentist.

Generally, in the preferred embodiment the steel casing is cylindrical, although it may have other tubular shapes. It has a wall thickness sufficient to provide adequate strength for manipulation and retraction and thus, in the stainless steel embodiment, has a wall thickness of at least 1/32 of a millimeter. Its tubular diameter is in the range of 3 millimeter to 20 millimeters, and in the preferred embodiment is 7 millimeters.

The plastic sheath 24 is a cylindrical tube in the preferred embodiment and serves the purpose of holding the air hose 28, the water hose 29 and light conductor 26 together but is flexible enough outside the handle 21 to permit easy manipulation of the handle 21. It may be polyvinyl chloride or any other suitable flexible sheathing material with sufficient strength to hold the air and water hoses and light conductor together.

The light conductor 26: (1 1 ) is conventional; (2) includes an inner core of one transparent material having one refractive index coated with an outer shell of a different refractive index to conduct light along its length; (3) is sufficiently thin to be flexible; and (4) in the preferred embodiment, includes polyvinyl chloride sheathing enclosing a 0.5 millimeter diameter bundle of light conductors. Its diameter should be small enough to permit easy insertion in the retractor 20A or probe 20 but different diameters of conductor may be used with a lens, not shown, to focus the light from a thicker bundle onto the narrower bundle for transmission through the retractor 20A or probe 20 (FIG. 2). A suitable fiber optic light guide may be purchased from Galleo Electo-Optics Corp., Galleo Park, Sturbridge, Mass. 01518.

The air hose 28, has a diameter of less than 4.0 millimeters and is adaptable to be connected to a standard dental hose adaptor but is of smaller diameter to fit easily within a relatively small space within the instrument handle casing 22. The major air hose 28 extends only to an outlet 42 near the retractor 20. Two smaller hoses (less than 0.5 millimeter diameter) extend on to the terminal end of the handle to be used to defog the visual aid (mirrors). In one embodiment, the handle 21 has a cut-away portion in which a button 27 is resiliently mounted, by which the small defogging hoses may be squeezed to reduce or terminate air flow but generally the flow of air and water is controlled externally of the retractor by controls that are standard on the commercially available equipment.

Figure 4:
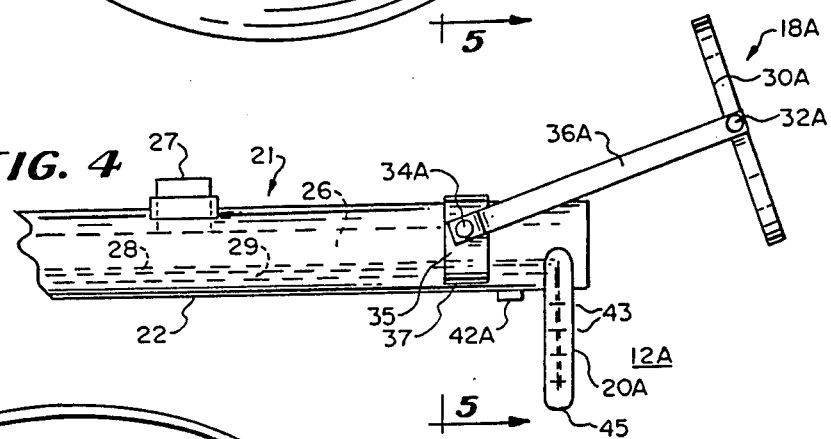
FIG. 4 is a fragmentary elevational view of another embodiment of probe assembly useful in the invention of FIG. 1.

In FIG. 4, there is shown another embodiment of probe 12A having another embodiment of mirror 30A mounted to it for pivotal action and a button 27. This embodiment of probe 12A includes a blade shaped retractor and this embodiment of mirror 30A includes a pivotal mirror support 32A, pivotal holder support 34A and mirror holder to be described in greater detail below to provide better adjustment of the mirror 30A. The button 27 may be depressed in some embodiments to restrict the flow of air. Retractor 20A is of the blade-shaped configuration.

Figure 5:
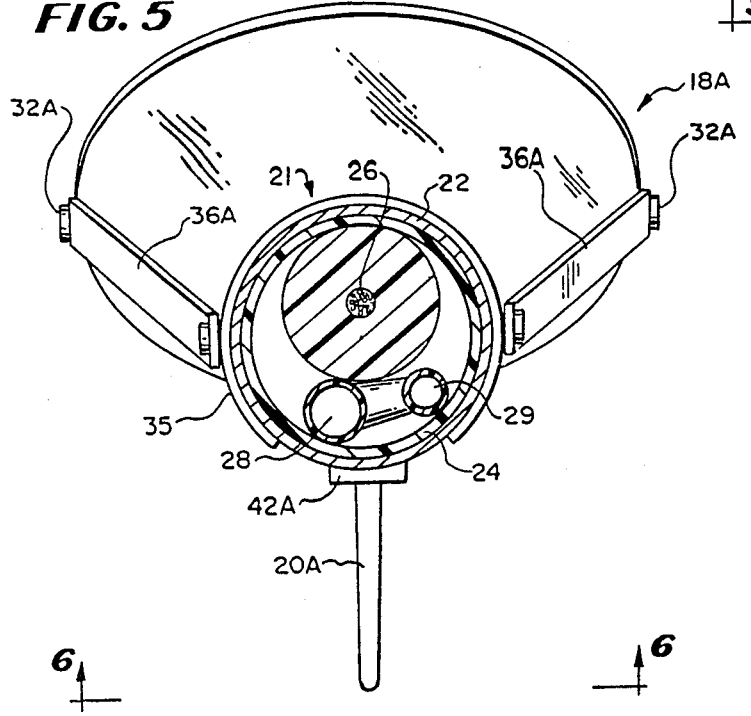
FIG. 5 is an enlarged sectional view taken through lines 5—5 of the probe assembly of FIG. 4.

In FIG. 5, there is shown a sectional view of the probe assembly 12 taken through lines 5—5 of FIG. 4, showing the handle 21, and an embodiment of mirror 30A (not labeled in FIG. 5 but in FIG. 4) similar to the mirror 30 (FIG. 2), and the retractor 20A. The probe assembly 12 is similar to the probe 20 (FIG. 2) but shaped as a plate rather than a tube. The mirror 30A includes a reflective surface shown in FIG. 5, two pivot points of the mirror support 32A on either side of it, two arms of the mirror holder 36A extending outwardly and inwardly to pivot points of the pivotal holder support 34A (not labeled in FIG. 5) on the split ring holder 35 mounted on handle 21. The split ring holder may also be rotated with finger pressure in this embodiment or moved forward or backward on the handle 22.

As best shown in FIG. 5, the dentist holding the handle 22 receives reflections from the surface of the mirror 30A to obtain an easy visualization. The mirror 30A may be pivoted about the points of the mirror support 32A to adjust the angle of viewing and may be moved as a body upwardly and downwardly with the arms of the mirror holder 36A pivoting about the pivot points 34A for further adjustment. The split clip may also be rotated or moved longitudinally about the handle 22. In this embodiment, the retractor 20A is blade shaped having slits 43A and 45 for emission of light (FIG. 4).

To provide for a flow of air and/or water over the tooth, the air hose 28 and water hose 29 are each connected to an exit orifice 42A. With this arrangment, air and water may exit as a spray from the opening 42A in a manner known in the art or only air may exit as selected under the control of a standard control box as known in the art.

In the embodiment of visual aid 18A (not shown in FIG. 2 but shown in FIGS. 4 and 5) the mirror 30A is removably supported and pivotable. It is removably mounted to the handle 21 by a split ring 35. It pivots at the pivot points 34A of the holder support by the arms of the mirror holder 36A which connect to the mirror 30A at the pivot points of the mirror support 32A to permit adjustment of the location of the pivot point of the mirror support 32A along an arc around the pivot point of the holder support 34A. The radius of the arc is as long as the arms of the mirror holder 36A.

The pivot point of the mirror support 32A permits adjustment of the angle of the mirror 30A with respect to the arms of the mirror holder 36A. With this arrangement, the visual aid 18 (FIG. 2) or 18A (FIGS. 4 or 5) is mounted to the handle 21 and positioned at an angle to permit easy viewing of a portion of the mouth by the dentist.

To permit retraction of tissue and illumination of selected locations, the probe 20 (FIG. 2) is, in the preferred embodiment, 15 millimeters long from the bottom of the handle 21 to the tip of the probe and should be at least three millimeters long and no longer than 30 millimeters. When shaped as a blade, the retractor 20A has a length extending downwardly from the handle, a width which is its longest dimension perpendicular to its length, and a thickness which is in a direction perpendicular to its width and length. In the preferred embodiment, the retractor length is 15 millimeters and it should be between 3 and 30 millimeters long.

The length of probe or retractor should be sufficient to fit within an 8 to 10 millimeter deep opening and the light guide should extend in the blade retractor sufficiently far to enter and illuminate the sulcus, and in the cylindrical probe, to enter and illuminate the pulp chamber. The light guide preferably goes to the tip of the retractor or probe where it can be brought into intimate contact with the surface of the tooth. This contact is sufficiently close so that more light flux is transmitted through the dentin within the tooth away from the tooth surface than reflected from the tooth surface.

One size cylindrical probe has a rounded tip with a diameter of 0.75 millimeters and a 0.50 millimeter diameter fiber optic light guide in its center. It should have a diameter of between 0.25 and 3.5 millimeters.

A blade shaped retractor has a thickness next to the handle of 1.3 millimeters and 0.95 millimeters at its rounded end with a 0.5 millimeter diameter light guide along its center and should have a thickness of between 0.25 millimeter and 2 millimeters. It has a width near the top in a direction paralled to the longitudinal axis of the handle of 4.2 millimeters and at its end of 2.5 millimeters and should be between 0.50 and 10 millimeters.

Thus, the largest dimension other than length of the retractor should be no longer than 10 millimeters (usually only for blade type) and a minimum of 0.25 millimeter. The retractors may be attached by a tongue and groove connection or welded or screwed or fastened in place by any suitable means.

In each of the embodiments of probe or retractor assembly 12, a corresponding probe or retractor 20 or 20A extends perpendicularly to and is rigidly connected to the handle 21 to permit use as a retracting blade as well as to provide illumination. Fluid flow is provided from an opening near the base of the retractor where it meets the handle. Light may pass through one or more slits or holes 43 (FIGS. 2 and 4) in the sheath or through an opening 45 in its end. The slits 43 are spaced 3 millimeters apart from each other throughout the length of the retractor 20 but may be omitted entirely or replaced by other shaped openings or spaced different distances.

For best results: (1 1 ) the retractor should be sufficiently strong in the directions substantially perpendicular to the handle 21 to permit retraction of gingival tissue; (2) the modulus of elasticity and yield point of the retractor should be sufficient so as not to bend more than 2 millimeters nor yield when a force between its tip and base and perpendicular to its axis of five pounds is applied; (3) the sheath 22 of the handle 21 should be sufficiently stiff and strong to prmit retraction of tissue without permanent deformation of the sheath (in the preferred embodiment, it is metal); and (4) the adaptor should be of such a size and configuration as to mate with standard sockets of hoses supplying air, water and light to other dental tools.

The hose connector section 23 includes an outer conical portion 47 and an externally threaded cylinder portion 49, separated by an annular shoulder 51. A sealing gasket 53 seals the end. A fiber optic connector 26A, an air connector 28A, for air at 30 psi (pounds per square inch) and a water connector 29A extend through the gasket for connection with a standard hose to supply light, air and water to the conductor 26, and hoses 28 and 29 respectively. A connector for air exhaust extends outwardly but is not functional except to permit use of a standard socket.

Figure 6:
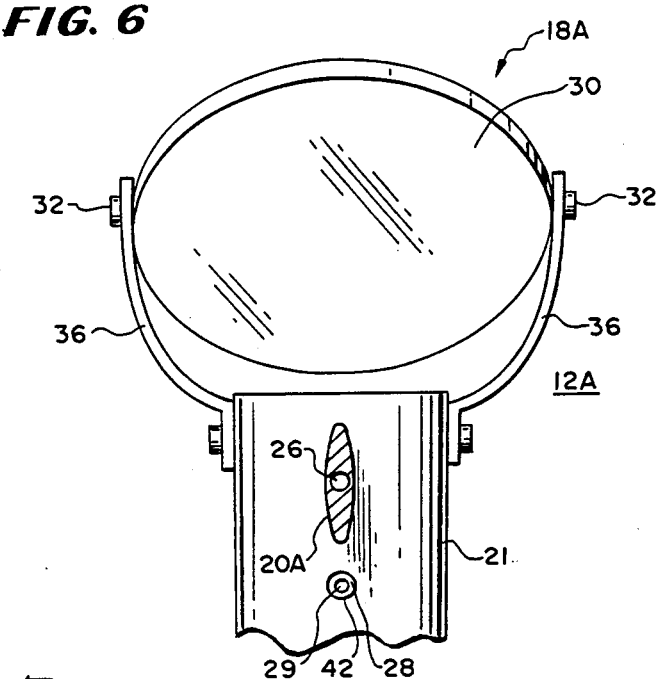
FIG. 6 is an enlarged, fragmentary sectional view taken of the probe assembly of FIG. 4.

In FIG. 6, there is shown a sectional view of the probe assembly 12 taken through lines 6—6 of FIG. 5 showing a portion of the handle 21, the mirror 30, and a section of the retractor 20A. The retractor 20A has an elliptical cross section and sufficient strength in compression to move within gingival crevices and sufficent bending strength and modulus of elasticity to permit retraction. As shown in this view, the retractor 20A has a light-passing interior which may contain the fiber optic bundle 26. It is relatively narrow to fit within the gingival crevice.

In FIG. 7, there is shown an elevational view of the light source 14 connected by a light source adaptor 50 to the light conductor 26. In one embodiment the light source 14 is manufactured as the Ultra-L by Star Dental Manufacturing Co., Inc., Conshohocken, Pa. 19428, and is sold by them under catalog number UL20/30G, 120F, 60 hertz, 2 amp. It includes at its outlet a metal disk 52 with three holes for receiving fiber bundles. The light source adaptor 50 will also easily couple with other widely available dental light sources.

The lamp must provide light of sufficient intensity to illuminate the dentin within a tooth some distance from the tooth surface. The light intensity from the probe or retractor should be at least 3.5 milliwatts and preferably 10 milliwatts per square millimeter and the lamp or other light source must be selected accordingly.

To transmit light from the light source 14 to the fiber bundles 26, the adaptor 50 contains a housing connectable at 52 to the light source by a set screw. The housing includes a lens 56 for focusing light onto the fiber bundle 26 to reduce the light output size from 2.0 millimeters diameter to the 0.50 millimeter diameter bundle 26. The bundle 26 fits into the adaptor hole to which it is molded in a tight connection and the adaptor fits into one of the outlet ports of the light source 14 which has a diameter of 2.4 millimeters. It extends into the outlet 22 millimeters.

In the preferred embodiment, the fiber optic bundle (0.5 millimeter diameter) extends in one piece from the end of the adaptor (22 millimeters into the outlet) to the probe tip (26, FIG. 6). At the light source end, the 0.5 millimeter diameter fiber optic bundle is contained in a metal housing adaptor 2.4 millimeters in diameter and 22 millimeters long (which fits into the light source connector 52). The fiber optic bundle is covered by a plastic sheath until it enters the master sheath 24.

In the preferred embodiment, the air hose 28 and water hose 29 are attached at their source end to a standard 4-hole adaptor which in turn is coupled with a standard 4-tube connection which traditionally supplies air and water to dental units. The flexible air hose 28 and water hose 29 extend a short distance before entering the master sheath 24B with the fiber optic bundle 26.

In the preferred embodiment, the air hose 28, water hose 29, and the fiber optic bundle 26 extend into the sheath 24B which holds them together and fits with them into the handle 21. With this arrangement, the light source and air and water sources are sufficiently spaced from the handle 21 (FIG. 2) to provide a relatively long flexible hose sufficient to permit ready and easy manipultion of the handle 21 (FIG. 2) by the dentist. This length should be at least 3 feet, ideally 6 feet.

Figure 8:
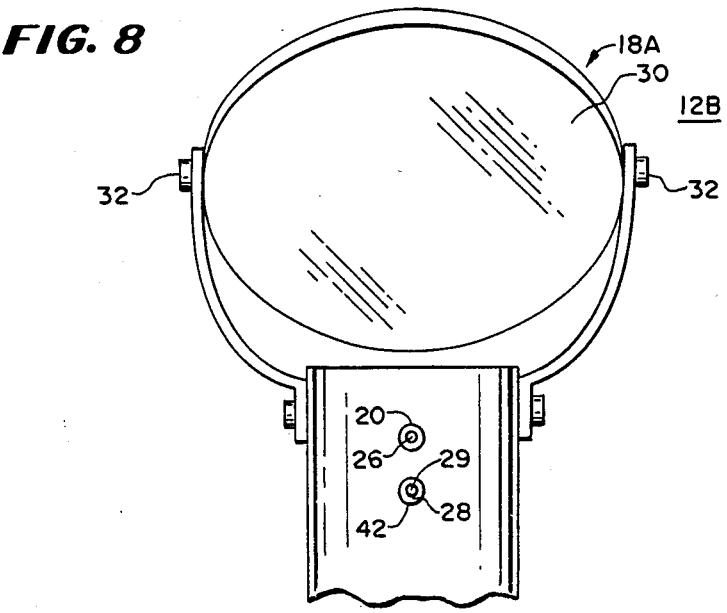
FIG. 8 is a fragmentary view of an embodiment of the probe assembly.

In FIG. 8, there is shown another embodiment 12B of probe assembly substantially the same as the probe assembly 12A except for the probe or retractor 20 itself, which is of the type shown in FIG. 2. The probe or retractor 20 in the embodiment of FIG. 8, instead of being blade shaped as is the retractor 20A (FIG. 6), is cylindrical and tubular having a cylindrical opening through which light from the light bundle 26 is emitted and, in one embodiment, slits (FIG. 2) (not shown in FIG. 8) along its length for the lateral emission of light. The probe assembly 12B of FIG. 8 is used in a manner similar to that of the probe assembly 20A (FIG. 5) and for that purpose, the probe or retractor 20 must have a diameter less than 2 millimeters and sufficient strength to withstand probing pressures into constricted areas of the oral cavity and sufficient length to fit within such cavities as pulp canals.

In the embodiment of probe assembly 12B, the visual aid 18A is the same or in the embodiment of FIGS. 4-6, and the outlet 42 is the same as in the embodiment of FIG. 2. It includes a central opening of approximately 0.55 millimeters (0.95 millimeters outer diameter) and is converted to the water hose 29 (FIGS. 2, 3 and 5) for the application of water surrounded by a 1.5 millimeter inside diameter annular opening for air connected to the tube 28. The air and water opening are focused at the retractor tip. Thus the fluid outlet forms an angle with the longitudinal axis of the handle which is within 10 degrees of the arc tangent of the retractor length divided by the distance from the outlets to the base of the retractor where it extends from the handle. It is less than 5 centimeters from the base of the retractor.

In FIG. 9, there is shown a source of light 14A, and connections for air and water 16 for application to the retractor assembly 12 (FIG. 1) through female socket 104 which engages male socket 47 of the hose connector section 23 (FIG. 2). It includes a connection 28A for air, connection 29A for water and 26A for light. The air exhaust connection need not be used. The connections to the standard dental sources of air and water are through a cord 31 which is preferably 6 feet long and at least 3 feet long. This equipment is conventional except: (1) as to its cooperation with the probe assembly 12 (FIGS. 1-8); and (2) in that a lamp is located at 14A in socket 104 to reduce attenuation so as to permit increased light intensity at the probe or retractor.

The lamp must provide light of sufficient intensity to illuminate the dentin within a tooth some distance from the tooth surface. The light intensity from the probe or retractor should be at least 3.5 milliwatts and preferably 10 milliwatts per square millimeter and the lamp or other light source must be selected accordingly.

In FIG. 10, there is shown an end view of the male connector 23 for connecting to the hose connector section 104 (FIG. 9) for supplying light through conductor 26, air through conduit 28 and water through conduit 29 (FIG. 3). This connector permits easy adaptation to existing dental offices. The connector 23 is a standard four-hole plus fiber optic connector configuration (Midwest, Star Dental). The fiber optic bundle extends 11 millimeters from back of handpiece when coupled with hose connector, section 104 (FIG. 9) and only 4 millimeters for the standard 4-tube plus fiber optic bundle connections.

In FIG. 11 there is shown the preferred embodiment of adaptor 23A having an air connector 28B and a water connector 29B, the remaining male connections being blank and not used except to fit the standard four-hole configuration. The adaptor 23A is a standard four-hole adaptor which may be purchased under Syntex (Star) number 57344 from Star Dental, P.O. Box 960, Valley Forge Corporate Center, Valley Forge, PA 19482.

The adaptor 23A supplies air and water through a flexible sheath 24B which receives a fiber optic bundle from the light source 14B and connects in a continuous piece into the handle 21 of casing 22 (FIG. 2) to supply light, air and water thereto. The flexible cord is at least 3 feet long and preferably 6 feet.

In FIG. 12, there is shown a female socket 104B for supplying the adaptor 23A with air under pressure and water. This is a standard four-hole configuration socket (Star) adapted to be connected to dental sources of air and water.

Figure 13:
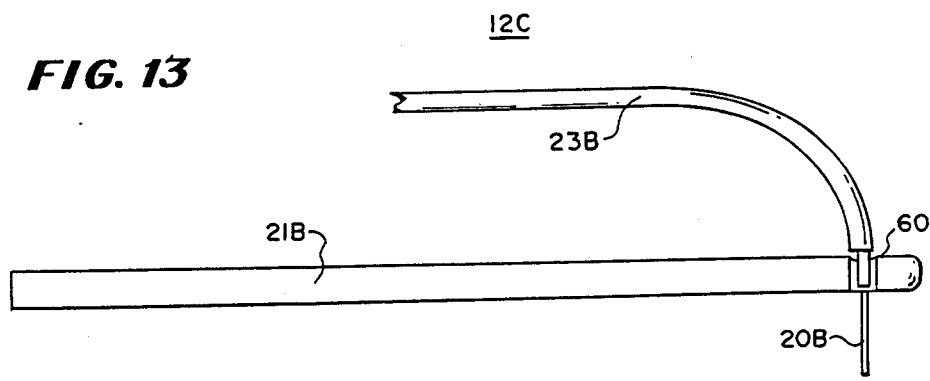
FIG. 13 is a fragmentary elevational view of still another embodiment of the probe assembly.

In FIG. 13, there is shown still another embodiment of retractor assembly 12C in which the flexible hose 23B and the rigid handle 21B are separate except at an aperture 60 in which the probe or retractor 20B fits into the handle 21B to hold the flexible portion 23B to the handle 21B. In this embodiment, the handle is a toothbrush holder sold under the trade name Proxabrush by J. O. Butler Co., Chicago, Ill., with an aperture drilled into it to receive a 20 millimeter base portion of the probe or retractor 20B sealed to it in any suitable manner.

Figure 14:
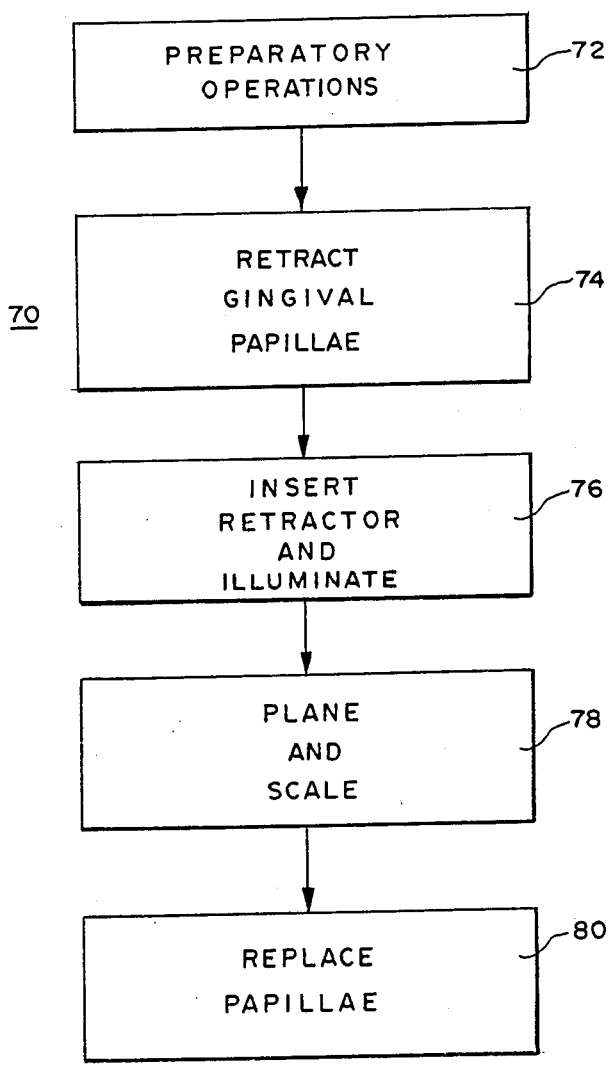
FIG. 14 is a block diagram of the method of dental viewing using the apparatuses of FIGS. 1–13.

In FIG. 14, there is shown a block diagram 70 illustrating one process of using the probe assembly 12 and including: (1) the step 72 of performing certain preparatory operations; (2) the step 74 of making a single diagonal incision across the gingival papillae and retracting the papillae only; (3) the step 76 of inserting the retractor 20A of the probe assembly 12 and illuminating or transilluminating and drying; (4) the step 78 of performing the planing and scaling operation; and (5) the step 80 of replacing the papillae.

Before commencing, a local anesthesia, including injections into the papillary areas for hemostasis is performed as shown at the step 72. An incision is made to free the gingival papillae only. The papillae may be retracted with a retractor 20A (FIG. 4).

The papillae is reflected with the blade-shaped retractor 20A to expose the interproximal root surfaces while minimally disturbing periodontal attachment. The root is flushed with air or water spray to remove blood and debris, then dried using the air nozzles which may be activated by a foot lever. Intense fiber optic light is applied through the retractor tip to illuminate and transilluminate accretions on the root surfaces.

As shown in step 78, scaling and root planing are now performed using a compact ultrasonic scaler of a type known in the art. Evacuation is accomplished with a patient-held saliva ejector and water lavage from the ultrasonic sonic scaler or probe assembly control hemorrhaging. With direct visualization and mechanical access, the scaler tip can be directed to all parts of the exposed root. Intermittent use of air from the air hose allows drying for detection of small pieces of remaining calculus. After the step 78 has been completed, the papillae are replaced and held under pressure with a wet gauze for three minutes as shown in step 80.

As can be understood from the above description, the method and apparatus for dental viewing with this invention has several advantages such as: (1) scaling and root planing and other similar operations may be performed by one operator; (2) less root planing skill and less skill with other operations are required of the operator because of the visual and mechanical access provided by the probe assembly 12 due to its intense light emission within the constricted area, small size and multiple functions; (3) more predictable results are obtained, particularly in more thorough root debridement in less time; (4) there is less soft tissue trauma because the tissues are held away from the scaling tip of the scaling instrument; (5) there is minimal post-operative discomfort; (6) no sutures or post-operative visits are normally required; (7) there is excellent soft tissue adaptation to the root; and (8) the need for more involved surgical procedures is reduced.

Although a preferred embodiment of this invention has been described with some particularity, many modifications and vaiations in the preferred embodiment are possible within the light of the above teachings. Therefore, it is to be understood that, within the scope of the appended claims, the invention may be practiced other than as specifically described.

What is claimed is:

1. Apparatus for dental viewing comprising:
dental instrument assembly means;
said dental instrument assembly means including an elongated handle and an elongated retractor having a retractor base, a retractor blade and a retractor edge;
said elongated handle having a longitudinal axis, the length of the elongated handle along the longitudinal axis being between 6 centimeters and 25 centimeters long;
said dental instrument assembly including means for guiding light through said elongated retractor to said retractor edge and means for providing fluid flow toward the retractor edge;
said elongated retractor having a longitudinal axis substantially at right angles to the longitudinal axis of said handle and having a length sufficient and a width and thickness small enough to enter dental access openings;
said elongated handle being tubular and adapted to be connected to a source of light, fluid and air;
said means for providing fluid flow toward the retractor edge including fluid outlet means for selectively applying air alone, liquid alone, both air and liquid and neither air nor liquid through said tubular handle in the direction of said retractor edge;
said outlet means being less than 5 centimeters from the base of the retractor blade and focused at the retractor edge;
said means for guiding light including a light conductor and source of light having an intensity of at least 3.5 milliwatts per square millimeter positioned to transmit light through the light conductor whereby the light when emitted has an intensity at least sufficient for transillumination;
said retractor having a thickness of between 0.25 millimeters and 2 millimeters, and a width of between 0.50 and 10 millimeters; and
said elongated retractor having a length of between 3 and 30 millimeters.

2. Apparatus according to claim 1 in which said handle means is cylindrical, is between 6 and 25 centimeters long and has a diameter of between 3 and 20 millimeters.

3. Apparatus according to claim 1 in which said fluid outlet has internal walls making an angle with the longitudinal axis of the handle which is within 10 degrees of the arc tangent of the retractor length divided by the distance of the fluid outlet port from the base of the retractor.

4. Apparatus according to claim 1 in which:
said tubular handle means receives within it a bundle of light fibers, an air hose and a water hose;
said bundle of light fibers extends from said handle to the retractor edge;
said light fibers communicating with the retractor and said water and air hoses communicating with orifice means for providing selected ones of air or air and water mixed in the direction of said retractor edge.

5. Apparatus for dental viewing comprising:
dental instrument assembly means;
said dental instrument assembly means including an elongated handle and an elongated tool having a tool base and tool tip;
said elongated handle having a longitudinal axis, the length of the elongated handle along the longitudinal axis being between 6 centimeters and 25 centimeters long;
said dental instrument assembly including means for guiding light through said elongated tool to said tool tip and means for providing fluid flow toward the tool tip;
said elongated tool having a longitudinal axis substantially at right angles to the longitudinal axis of said handle and having a length sufficient and a diameter of the elongated tool adjacent to the tool tip small enough to enter dental access openings;
said elongated handle being tubular and adapted to be connected to a source of light, fluid and air;
said means for providing fluid flow toward the tool tip including fluid outlet means for selectively applying air alone, liquid alone, both air and liquid and neither air nor liquid through said tubular handle in the direction of said tool tip;
said outlet means being less than 5 centimeters from the base of the tool and focused at the tool tip;
said means for guiding light including a light conductor and source of light having an intensity of at least 3.5 milliwatts per square millimeter positioned to transmit light through the light conductor whereby the light when emitted has an intensity at least sufficient for transillumination;
said tool tip being a cylindrical probe having a diameter of less than 3.5 and more than 0.25 millimeters.

6. A method of tooth scaling comprising the steps of:
applying local anesthesia at least to papillary areas;
surgically freeing gingival papillae;
reflecting the papillae with a dental instrument assembly means having an elongated handle of between 6 and 25 centimeters long and a diameter of between 3 and 20 millimeters and having an elongated retractor tool with a retractor base, a retractor edge and a retractor blade with a thickness of between 0.25 millimeters and 2 millimeters, a width of between 0.50 and 10 millimeters, and a length of between three and 30 millimeters until interproximal root surfaces are exposed;

applying a spray of air and water together and air alone toward said retractor edge from outlet means spaced less than 5 centimeters from the retractor base and focused upon the retractor edge to rinse and to dry the dental roots;

applying light through the elongated retractor tool to the retractor edge to permit transillumination and illumination of accretions on the root surface during air drying;

scaling the root surface;

reevaluating root surface cleanliness with water spray, air drying and light application from the retractor edge;

replacing the papillae and holding under pressure;

the step of reflecting including the step of reflecting with the retractor blade attached at a right angle to the handle which receives through it and supplies the retractor blade with light to be transmitted through the blade edge.

* * * * *